United States Patent [19]
Chevalier

[11] Patent Number: 5,425,273
[45] Date of Patent: Jun. 20, 1995

[54] FIBER OPTIC PRESSURE SENSOR WITH INCLUSIONS IN A COMPRESSIBLE TRANSPARENT MATERIAL

[75] Inventor: Philippe Chevalier, Nazareth, Belgium

[73] Assignee: Cosurvey Optics, Brussels, Belgium

[21] Appl. No.: 30,350
[22] PCT Filed: Jul. 26, 1991
[86] PCT No.: PCT/BE91/00052
§ 371 Date: Aug. 3, 1993
§ 102(e) Date: Aug. 3, 1993
[87] PCT Pub. No.: WO92/02796
PCT Pub. Date: Feb. 20, 1992

[30] Foreign Application Priority Data
Jul. 27, 1990 [BE] Belgium .................. 9000752

[51] Int. Cl.6 ............ G01L 9/00; G01D 5/34; A61B 5/0215
[52] U.S. Cl. ............... 73/705; 250/231.19; 128/675
[58] Field of Search ............ 250/227.21, 231.19; 128/664, 665, 666, 667, 673, 675, 748; 73/705

[56] References Cited

U.S. PATENT DOCUMENTS

| | | |
|---|---|---|
| 3,273,447 | 9/1966 | Frank . |
| 4,599,908 | 7/1986 | Sheridan et al. ........... 250/227.21 X |
| 4,691,709 | 9/1987 | Cohen ..................... 128/667 |
| 5,173,432 | 12/1992 | Lefkowitz et al. .......... 128/665 X |
| 5,293,780 | 3/1994 | Chadwick et al. ............ 73/731 X |

FOREIGN PATENT DOCUMENTS

| | | |
|---|---|---|
| 0178806 | 4/1986 | European Pat. Off. . |
| 56-7034 | 1/1981 | Japan . |
| 2234344 | 1/1991 | United Kingdom . |

OTHER PUBLICATIONS
Patent Abstracts of Japan, vol. 12, No. 188 (P-711) (3035).

Primary Examiner—Richard E. Chilcot, Jr.
Assistant Examiner—Joseph L. Felber
Attorney, Agent, or Firm—Jacobson, Price, Holman & Stern

[57] ABSTRACT

A pressure sensor for connection to a transmission optical fiber which allows the transmission of a light beam. The pressure sensor comprises a material which is essentially elastic to deformation and optically transparent to the wavelengths of light used. The material includes at least two inclusions, each comprising an optical fiber segment. The distance between the inclusions varies when a deformation is exerted on the pressure sensor. This, in turn, modifies the focal length of the optical system defined thereby, and leads to a variation of the light energy collected by a transmissive optical fiber. The pressure sensor is suitable for detectors or measuring devices for medical use, and in this regard, a method for measuring blood or respiratory pressure is also provided.

9 Claims, 4 Drawing Sheets

FIBER OPTIC PRESSURE SENSOR WITH INCLUSIONS IN A COMPRESSIBLE TRANSPARENT MATERIAL

SUBJECT OF THE INVENTION

The present invention relates to a pressure sensor using optical fibers for transmission by light beams and extends to detection or measurement devices fitted with such a sensor.

DESCRIPTION OF THE PRIOR ART

Optical fiber pressure sensors may be classed in two categories, namely extrinsic and intrinsic sensors.

In extrinsic sensors, the optical fiber is passive and is only employed to transmit light from one point to another. In intrinsic sensors, the optical fiber is active and is employed for physical magnitude (pressure, temperature, pH, etc.) quantification.

U.S. Pat. No. 4,691,709 (Cohen) describes the pressure sensor capable of measuring blood speed and static pressure. This sensor is based on light energy losses resulting from the contact of an elastic foam with the optical fiber. The losses increase as a function of the widening of the contact zone.

This mode of operation is to be described as intrinsic since the basic characteristic of the optical fiber, total reflection, is altered in contact with the foam.

This sensor also makes use of the extrinsic mode of operation since it employs a reflecting membrane disposed at the end of the optical fiber and whose radius of curvature varies as a function of pressure.

However, if it is desired to mass produce this sensor, the positioning of this membrane in the sensor gives rise to technological problems whose cost implications are not negligible.

Patent Application JP-A-62,294,928 (Idemitsu Kosan Co. LTD) describes an optical attenuator measuring pressure on the basis of the variation in the transmission of the system.

The attenuator consists of a dispersion of colorant in an elastomer. The spatial distribution of the particles of colorants is modified by the pressure exerted on the elastomer such that a variation in the transmission of the system results therefrom.

This extrinsic sensor is for the most part based on a transfer function defined by the Behr-Lambert [sic] law, which amounts to saying that this function is of the $\exp(-ax)$ type in which a is the attenuation coefficient and x is the optical path covered by the light beam.

However, in mass production, such a sensor cannot guarantee a reproducible distribution of the colorant in the elastomer and consequently a reproducible configuration of the sensor cannot be obtained.

Furthermore, such a transmission sensor does not provide a sufficiently high signal/noise ratio and is difficult to transpose to a blood pressure measurement because of the necessary bulk.

Pressure sensors making use of optical fibers, and whose general operation is based on the displacement of mirrors fixed to membranes or to pistons subjected to pressure forces, are also known. [Scheggi (Institut di Ricerca Sulle Onde Elettromagnetische [sic] CNR-Firenze, Italy) and Matsumoto (J. Med. Eng. and Tech. 2, 239 (5) Sept. 1978)].

The displacement of the mirrors modifies the distribution of the light intensity in the optical fiber and thus makes it possible to measure the pressure exerted on the membrane or on the piston.

Patent Application EP-A-0178806 (Sperry Corporation) describes a pressure sensor of the intrinsic type using a 2×2 coupler in which the energy ratio of the output channels is influenced by the variation in the refractive index as a function of pressure.

Pressure sensors employing bifurcated optical fibers in which one end is connected to a membrane are known.

Instead of relying on the displacement of a membrane, Patent Application JP-A-56,7034 (Tokyo Shibaura Denki K. K.) describes a sensor using the radius of curvature of the reflecting membrane. The radius of curvature of the membrane varies in this case as a function of pressure.

U.S. Pat. No. 3,273,447 (Frank) describes an optical fiber terminated by a bulb made of material which is elastic to deformation and which can be covered with a reflecting layer.

This bulb has an aspheric shape and has been prestressed as a function of the pressure to be measured and as a function of the elastic characteristics of the material. As a function of the pressure exerted, the bulb deforms and reflects the light in the optical fiber to a greater or lesser extent.

According to one embodiment variant, a cavity may be introduced into this bulb. The cavity receives an aspheric shape such that a light beam follows a path around the cavity and is returned into the optical fiber.

Any pressure exerted on the bulb has the effect of increasing optical losses by virtue of the fact that the beam will no longer be totally reflected at certain locations on the surface, since the radius of curvature will have changed at these locations.

However, such a sensor has the disadvantages of providing insufficient sensitivity and of having a nonreproducible configuration when it is mass produced.

AIMS OF THE INVENTION

The present invention aims to provide a sensor with a very low cost price in comparison to those currently in use.

Another aim of the present invention is to provide pressure sensors which are suitable for medical applications, which therefore satisfy criteria of low size, which can be implanted, and which are therefore tolerated by the body.

Another aim of the present invention is to provide a pressure sensor with sufficient precision and reliability for a medical application.

An additional aim of the present invention is to provide a pressure sensor which has a configuration which is reproducible in mass production.

CHARACTERIZING ELEMENTS OF THE INVENTION

The invention essentially relates to a pressure sensor which can be connected to an optical fiber allowing the transfer of a light beam and which consists of a material which is essentially elastic to deformation and optically transparent to the wavelengths used, preferably an elastomer, comprising at least one inclusion consisting of at least one segment of optical fiber and whose transfer function is modified under the effect of deformation.

According to the invention, the inclusion has a circular cross-section, preferably of cylindrical shape and has a diameter between 10 μm and 500 μm.

This inclusion may consist of organic or inorganic glass, of a fluid and/or of a different elastomer from the elastomer surrounding the said inclusion.

Advantageously, the segment of optical fiber has an axis of rotation forming an angle with the axis of rotation of the said optical fiber allowing the transfer of light beams. This angle is preferably of the order of 90°.

BRIEF DESCRIPTION OF THE FIGURES

FIG. 4b represents a plan view of a preferred embodiment of the sensor according to the invention, corresponding to FIG. 4a.

DESCRIPTION OF A PREFERRED MODE OF THE INVENTION

Figure 1:
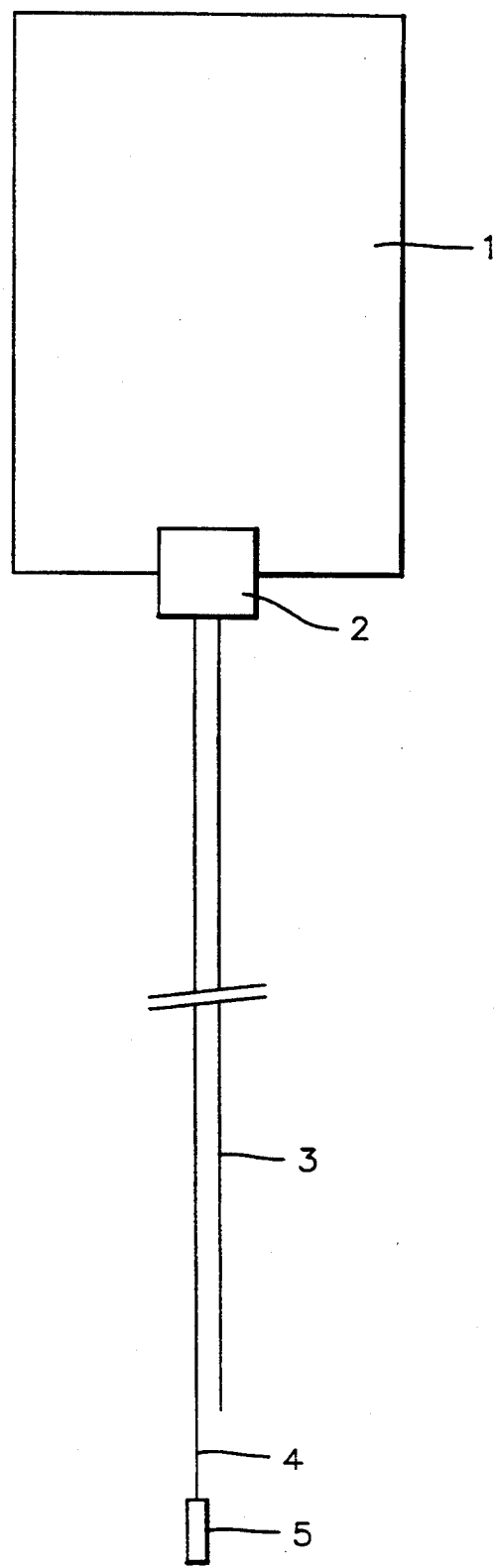
FIG. 1 represents a schematic view of the conventional detection system comprising a pressure sensor.

FIG. 1 represents a schematic view of a conventional detection system.

Figure 2:
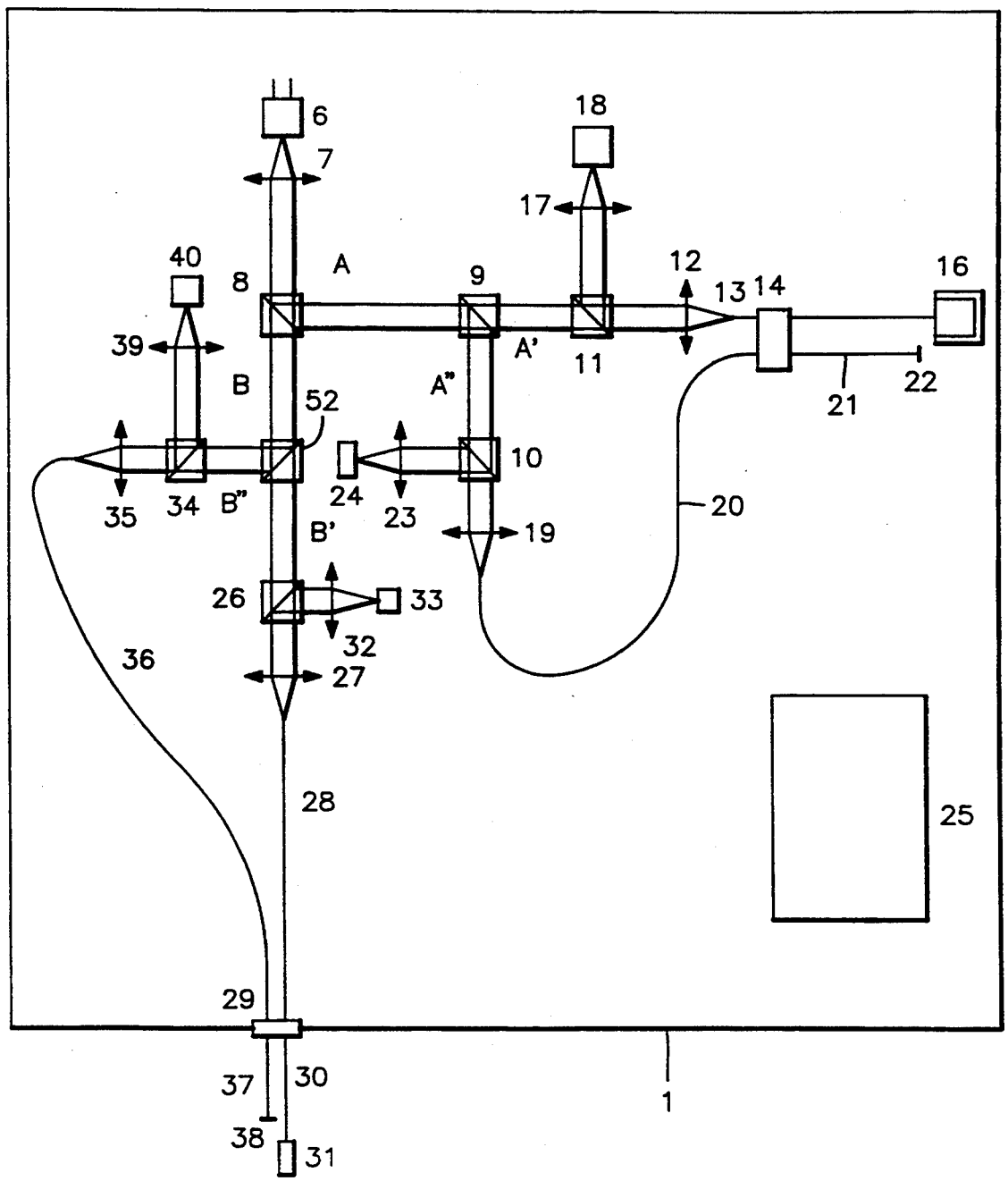
FIG. 2 represents the detection module in detail in accordance with the present invention.

The reference number 1 represents the detection module which is represented in greater detail in FIG. 2.

In order to obtain reliable measurement, it is conventionally necessary constantly to effect a compensation in order to eliminate the signals coming from a modification of the intrinsic parameters of the transmission fibers and other perturbations of the signal.

For this purpose, a so-called compensation fiber 3 is provided and is disposed in parallel with the transmission fiber 4 at the end of which the pressure sensor 5 is placed.

At the end of the compensation fiber 3 there is disposed a mirror which allows total reflection of the light ray.

An optical fiber connector 2 allows the two optical fibers 3 and 4 to be connected and removed.

According to a first embodiment, it is generally preferred to work in reflection. But it is also possible to envisage operation of the pressure sensor by optical fiber in transmission of the light beam.

Any pressure exerted on the sensor is converted into a modification of the light intensity reflected and/or scattered in the transmission optical fiber.

The light beam originates from a light emitter source 6 (laser/LED). The initial beam is collimated by the lens 7 and then split into two beams A and B by a splitter 8.

The beam A is split by a splitter 9 into A' and A".

The beam A' passes through a splitter 11 and is focused by a lens 12 onto an optical fiber 13. This optical fiber is connected to the connector 14. An optical fiber 15 conducts the light beam to a pressure sensor 16. This pressure sensor is placed under calibrated pressure. The signal is partially reflected by inclusions in the sensor as described hereinafter, and is returned by this sensor the optical fiber 15. The signal is then transmitted by the connector 14 to the optical fiber 13. This beam is then collected by the lens 12 and transmitted through the splitter 11 to the lens 17. The beam is then focused on the photodiode 18.

The beam A" is transmitted to the splitter 10 and is then focused by the lens 19 in the optical fiber 20. The optical fiber 20 is joined to the connector 14 and the beam is transmitted to the optical fiber 21. This optical fiber 21 is parallel to the optical fiber 15 and the optical fiber 21 is terminated by a mirror 22.

The beam is reflected by the mirror 22 and transmitted by the fiber 21 through the connector 14 into the optical fiber 20. The lens 19 picks up the beam and transmits it through the splitter 10 to the lens 23. The lens 23 focuses the beam on the photodiode 24.

The signals coming from the photodiodes 18 and 24 are processed by a processor 25. The principal operation performed by the processor is of calculating the ratio between the two signals.

The internal calibration is based on the recording of the signal as a function of the pressure exerted on the sensor 16. This function is stored.

A working pressure is chosen and this will be the basis for determining the difference between the signal generated by the sensor 16 and the sensor 31. During calibration, the sensors 31 and 16 are placed under the same pressure.

The beam B is split by a splitter 52 into B' and B". The beam B' passes through a splitter 26 and is focused by a lens 27 on an optical fiber 28. This optical fiber is connected to the connector 29. An optical fiber 30 conducts the light beam to a pressure sensor 31. Such a pressure sensor may be implanted on a patient. The signal coming from this sensor is returned into the optical fiber 30 and transmitted by the connector 29 to the optical fiber 28. The beam is then collected by a lens 27 and transmitted through the splitter 26 to the lens 32. The beam is then focused on the photodiode 33.

The beam B" is transmitted to the splitter 34 and is then focused by the lens 35 in the optical fiber 36. The optical fiber 36 is linked to the connector 29 and the beam is transmitted to the optical fiber 37. This optical fiber 37 is parallel to the optical fiber 30 and the optical fiber 37 is terminated by a mirror 38.

The beam is reflected by the mirror 38 and transmitted by the fiber 37 through the connector 29 into the optical fiber 36. The lens 35 picks up the beam and transmits it through the splitter 34 to the lens 39. The lens 39 focuses the beam on the photodiode 40.

The signals coming from the photodiodes 33 and 40 are processed by a processor 25. The principal operation performed by the processor is of calculating the ratio between the two signals.

The processor will finally process the signals coming from the photodiodes 18, 24, 33 and 40 in order to extract the pressure value therefrom.

Figure 3:
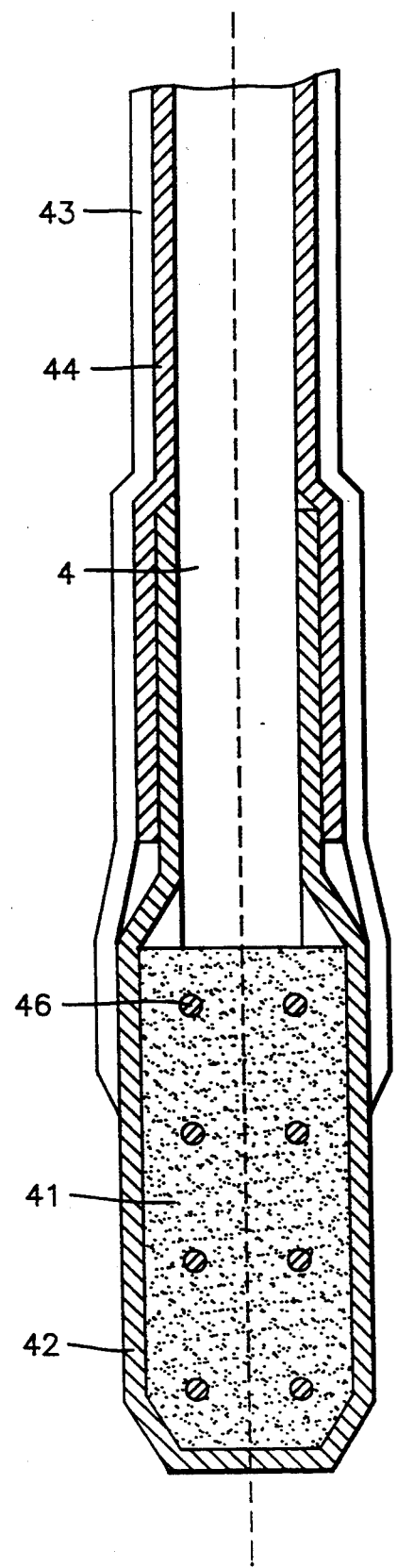
FIG. 3 represents a longitudinal section of the pressure sensor according to the present invention.

FIG. 3 represents a longitudinal section of a pressure sensor according to the invention which may be incorporated in a device of the type described hereinabove.

An elastomer block 41 and the optical fiber 4 are adhesively bonded together. A thin protective membrane 42, for example made of latex, covers the hole of the sensor. A sleeve 44 is used in order to fix the jacket 42 to the optical fiber 4.

The sensor is preferably made of a silicone. Since these sensors are more particularly intended for medical applications, for example for measuring blood or respiratory pressure, it is necessary for the pressure sensor to be placed in a catheter 43 which is tolerated by the human body. In general, this catheter consists of a latex jacket. It is obvious that for such an application, the dimensions of such a sensor must also be such that they can be tolerated by the human body in implant form, that is to say of the order of a millimeter.

The pressures detected by the sensors according to the invention are between 0 and 300 mm of mercury.

Figure 4A:
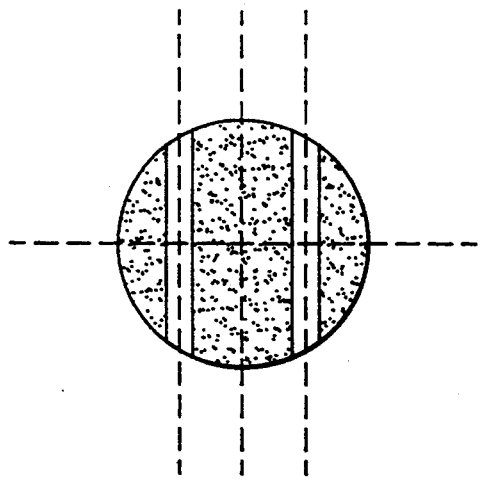
FIG. 4a represents a cross section of a preferred embodiment of the sensor according to the invention.
Figure 4B:
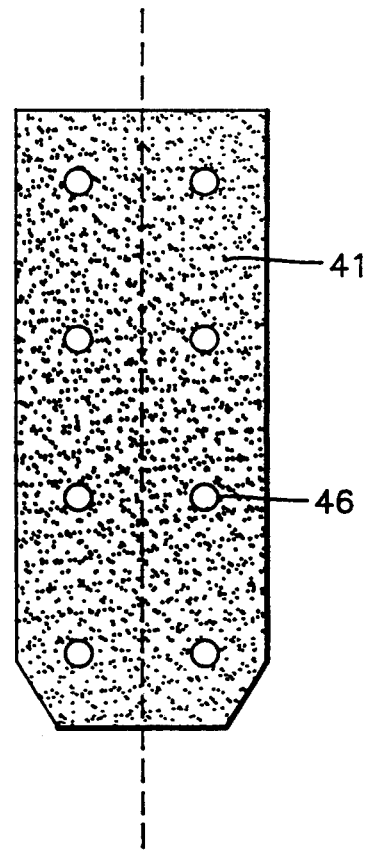

FIGS. 4a and 4b represent a preferred embodiment of the sensor according to the invention.

The sensor consists of a silicone block 41 in which there appear inclusion in the form of small cylinders 46 of silica optical fiber disposed essentially perpendicular to the light beam. The light ray emitted undergoes reflection, scattering and focusing phenomena. When a pressure is exerted on the sensor, the distance between the inclusions varies and by virtue of this, the focal length of the optical system varies, which leads to a variation in the light energy collected by the transmission fiber.

Although the drawings show cylindrically shaped inclusions, other shapes with a circular cross-section can be used. Preferably, the cylinders 46 have a diameter between 10 μm and 500 μm.

The inclusions may consist of organic or inorganic glass, or a fluid and/or of a different elastomer from the elastomer surrounding the inclusion.

Figure 5:
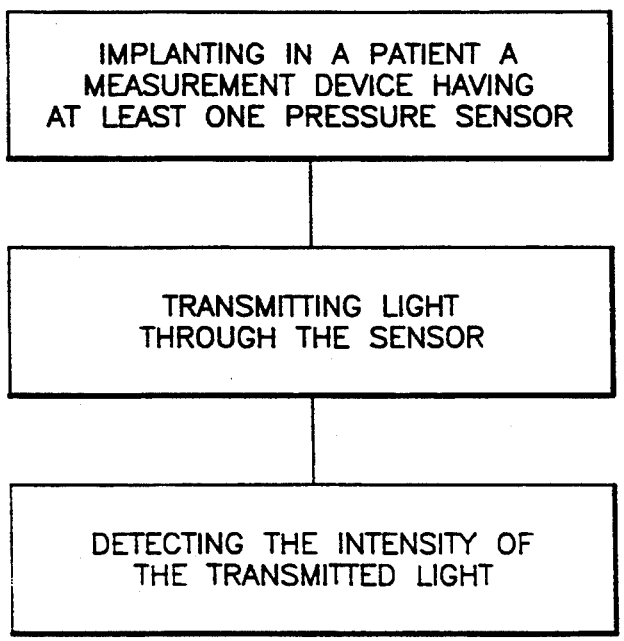
FIG. 5 is a flow chart illustrating a method for measuring blood or respiratory pressure according to the present invention.

It is evident that the present invention is not limited to the embodiment examples which are given solely by way of illustration. In particular, the present invention is not limited to medical applications such as those previously described and illustrated in FIG. 5.

It is also possible to envisage numerous other technological and industrial applications in widely varying fields, such as the measurement of vibrations in machines, traffic density, speed measurement during sports competitions, detection of security parameters of bridges and of works of art, etc.

I claim:

1. A pressure sensor which can be connected to a transmissive optical fiber allowing the transfer of a light beam, said pressure sensor comprising a material which is essentially elastic to deformation and optically transparent to wavelengths of said light beam, said material comprising at least two inclusions, each of said at least two inclusions consisting of an optical fiber segment, each inclusion of said at least two inclusions being separated by a distance from another inclusion which varies whenever there is deformation of the pressure sensor thereby modifying a focal length of an optical system defined by the combination of said at least two inclusions and said material of the pressure sensor which, in turn, provides variations in light energy being reflected back through the pressure sensor.

2. A sensor according to claim 1, characterized in that the essentially elastic material consists of an elastomer.

3. The sensor according to claim 1, characterized in that each of said at least two inclusions has a circular cross-section.

4. The sensor according to claim 3 characterized in that each of said at least two inclusions is of cylindrical shape.

5. The sensor according to claim 4, wherein each of said at least two inclusions has a cylindrical axis forming an angle with a longitudinal axis of said optical fiber allowing the transfer of light beams.

6. The sensor according to claim 5, characterized in that the said angle is of the order of 90°.

7. The sensor according to claim 1, wherein each of said at least two inclusions has a diameter between 10 and 500 μm.

8. The sensor according to claim 1 characterized in that each of said at least two inclusions chosen from a group consisting of organic or inorganic glass, fluid, or an elastomeric material different from the material surrounding each of said at least two inclusions.

9. A detection or measurement system comprising:
   a pressure sensor which can be connected to a transmissive optical fiber allowing the transfer of a light beam, said pressure sensor comprising a material which is essentially elastic to deformation and optically transparent to wavelengths of said light beam, said material comprising at least two inclusions, each of said at least two inclusions consisting of an optical fiber segment, each inclusion of said at least two inclusions being separated by a distance from another inclusion which varies whenever there is deformation of the pressure sensor thereby modifying a focal length of an optical system defined by the combination of said at least two inclusions and said material of the pressure sensor which, in turn, provides variations in light energy being reflected back through the pressure sensor; and
   means for transmitting said light beam into said transmissive optical fiber and detecting said light energy reflected back through the pressure sensor.

* * * * *